United States Patent
Webster, Jr. et al.

[11] Patent Number: 5,843,076
[45] Date of Patent: Dec. 1, 1998

[54] CATHETER WITH AN ELECTROMAGNETIC GUIDANCE SENSOR

[75] Inventors: Wilton W. Webster, Jr., Altadena; Dean M. Ponzi, Glendora, both of Calif.

[73] Assignee: Cordis Webster, Inc., Diamond Bar, Calif.

Related U.S. Application Data

[60] Provisional application No. 60/000,157 Jun. 12, 1995.

[21] Appl. No.: 662,360
[22] Filed: Jun. 12, 1996
[51] Int. Cl.⁶ .................................................. A61B 17/36
[52] U.S. Cl. .................. 606/41 D; 607/101; 607/122; 600/439; 604/95; 606/46
[58] Field of Search .................. 606/41, 42, 45–50; 607/100–102, 115, 116, 122; 604/95; 128/642, 653.1, 653.2, 653.4, 654, 660.01, 660.03; 600/374, 437, 439

[56] References Cited

U.S. PATENT DOCUMENTS

| | | |
|---|---|---|
| Re. 34,502 | 1/1994 | Webster, Jr. . |
| 4,699,147 | 10/1987 | Chilson et al. . |
| 4,960,134 | 10/1990 | Webster, Jr. . |
| 5,078,714 | 1/1992 | Katims ..................................... 606/38 |
| 5,172,699 | 12/1992 | Svenson et al. ........................... 606/46 |
| 5,222,501 | 6/1993 | Ideker et al. ........................ 128/660.03 |
| 5,364,352 | 11/1994 | Cimino et al. . |
| 5,391,199 | 2/1995 | Ben-Haim .............................. 607/122 |
| 5,395,328 | 3/1995 | Ockuly et al. . |
| 5,409,006 | 4/1995 | Buchholtz et al. ................. 128/660.03 |
| 5,431,168 | 7/1995 | Webster, Jr. ............................. 128/658 |

*Primary Examiner*—Michael Peffley
*Attorney, Agent, or Firm*—Christie, Parker & Hale, LLP

[57] ABSTRACT

The present invention relates to an electrophysiology catheter (an electrode catheter) having an electromagnetic sensor designed internally into the tip portion. The catheter is a size 7 French or 8 French of metal braided construction with preferably three lumens. The catheter has a deflectable tip utilizing an offset lumen with a puller wire, a non compressible coil in the body section and a compressible Teflon sheath in the tip section. The coil is glued to the catheter shaft at both ends of the coil but does not run through the deflectable section, thus deflection of the puller wire which deflects the tip to the coil, keeps the body from compressing and deflecting. The puller wire is soldered to a tip electrode and runs to a control handle. The electromagnetic sensor is mounted internally in the catheter tip by a combination of a hole drilled in the three lumen tip and a hollow bridging that covers the electromagnetic sensor and connects the tip electrode to the catheter shaft. Optionally mounted on the bridging tube are one or more ring electrodes adjacent to the tip electrode. The tip electrode is secured to the end of the bridging tube by an etched Teflon ring which mates the electrode stem to the inside of the ring.

26 Claims, 5 Drawing Sheets

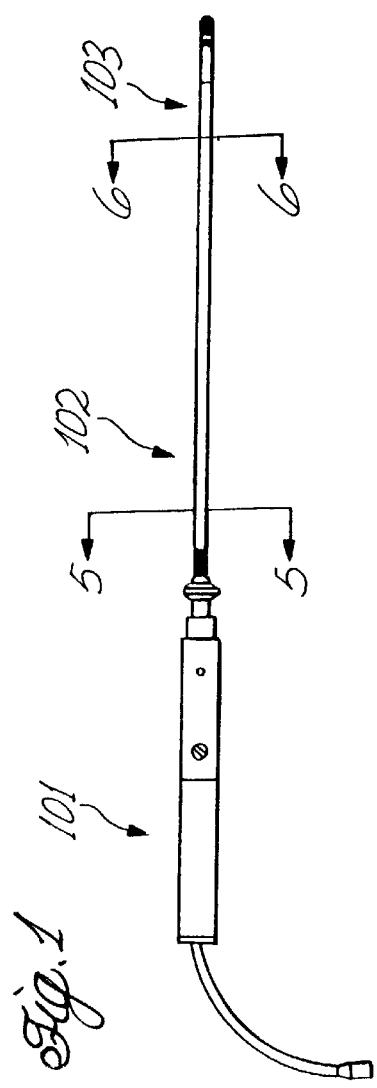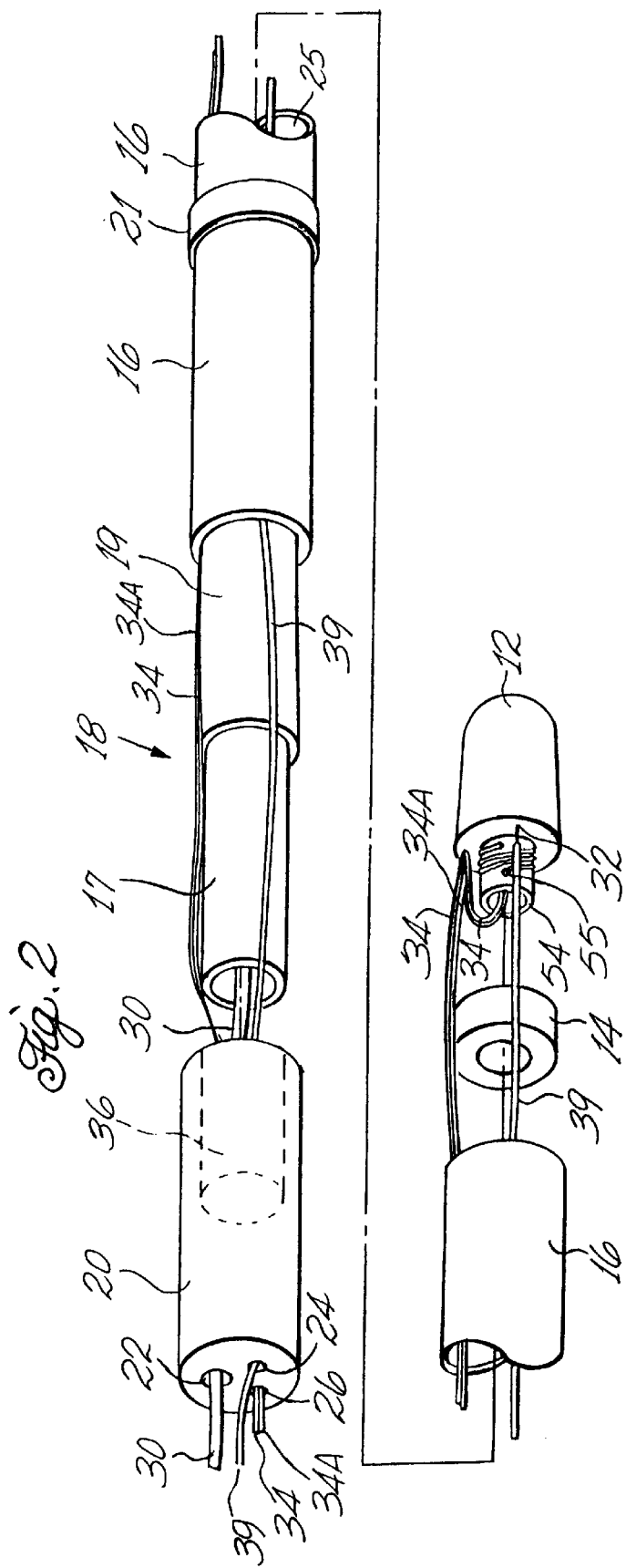

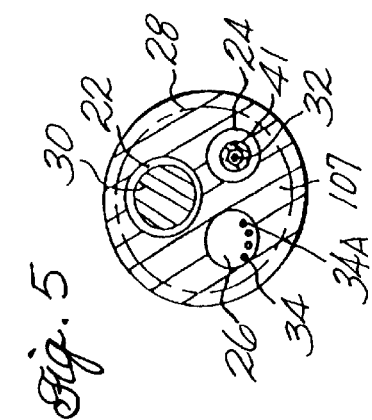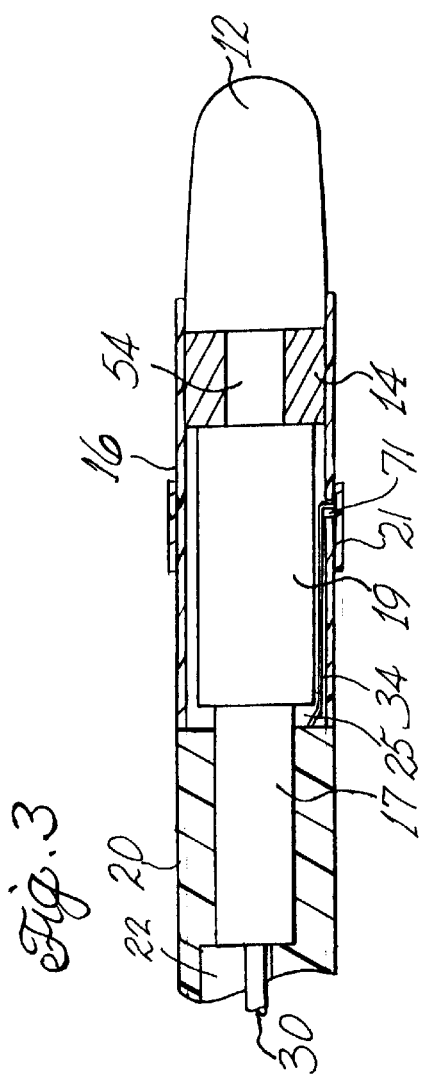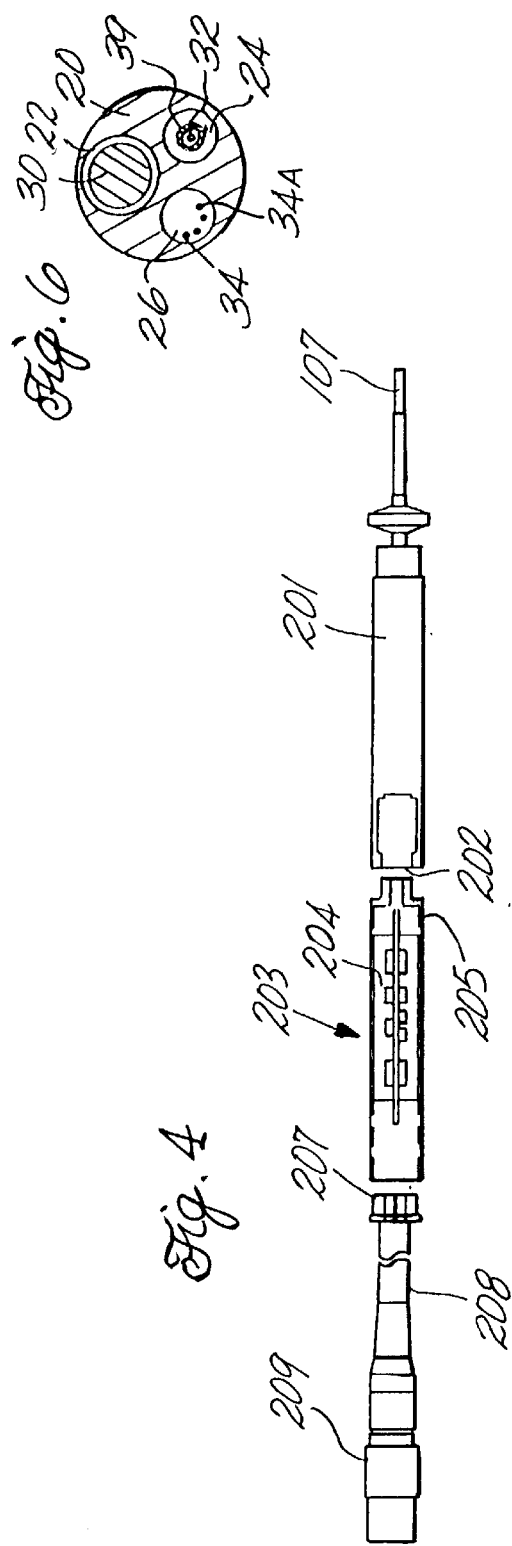

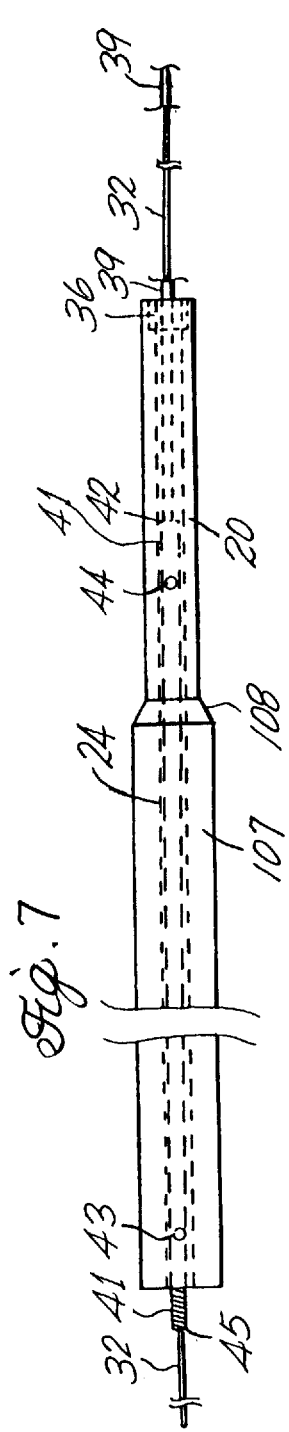
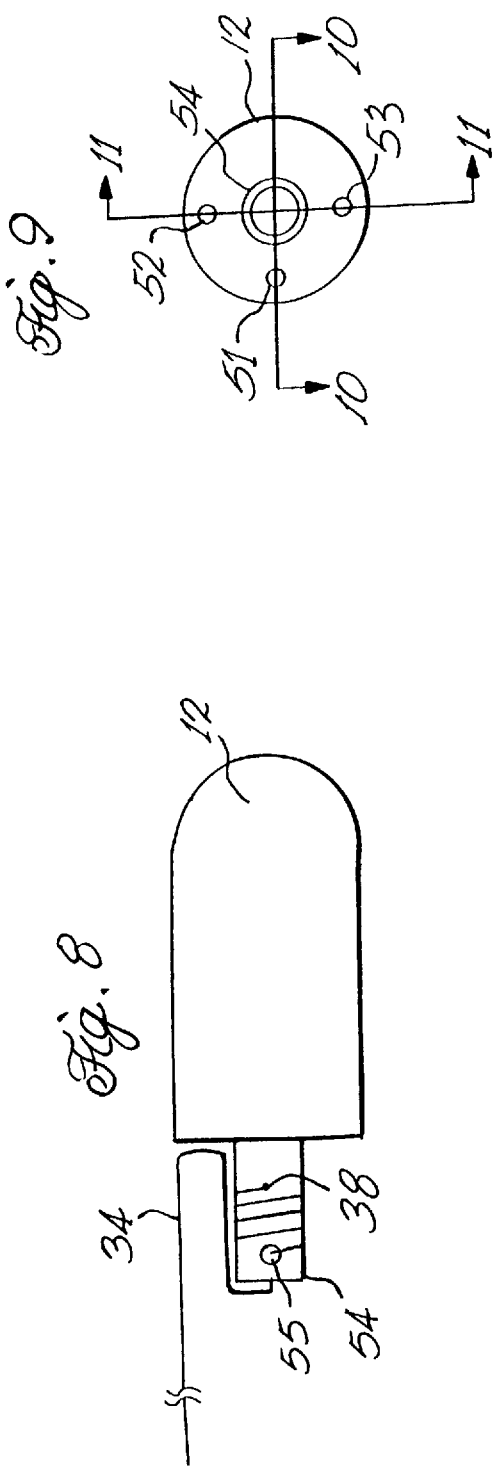

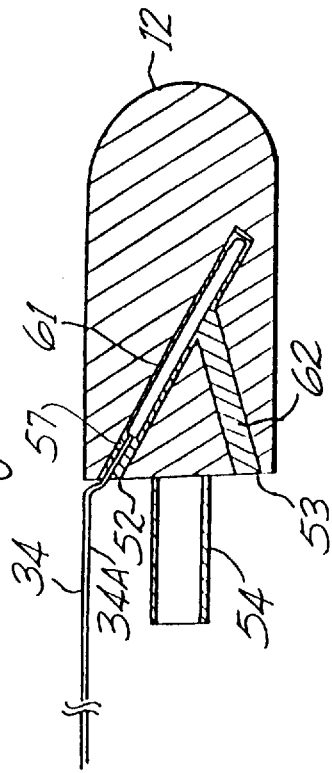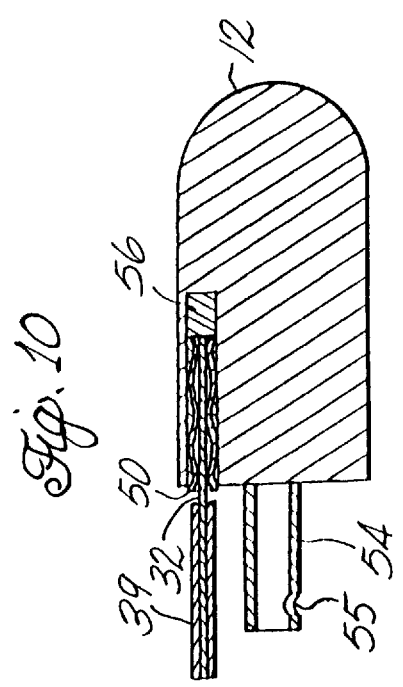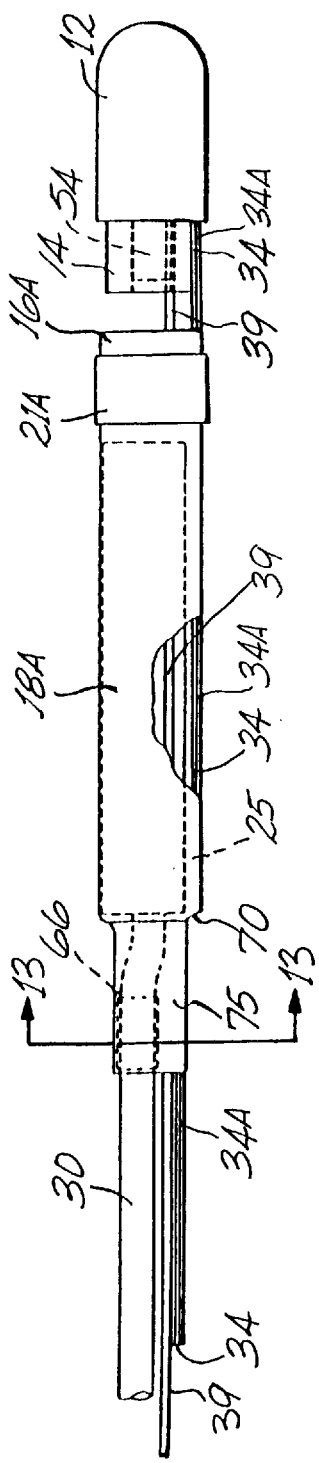

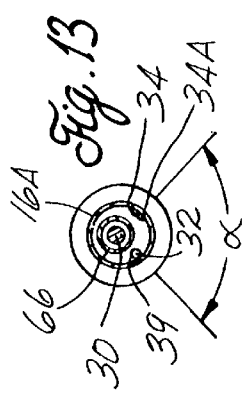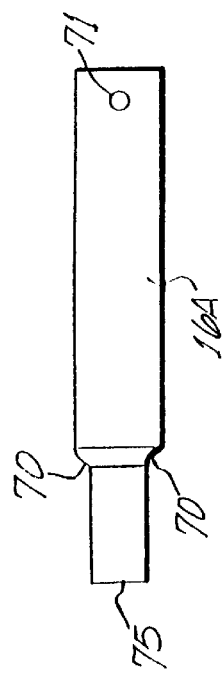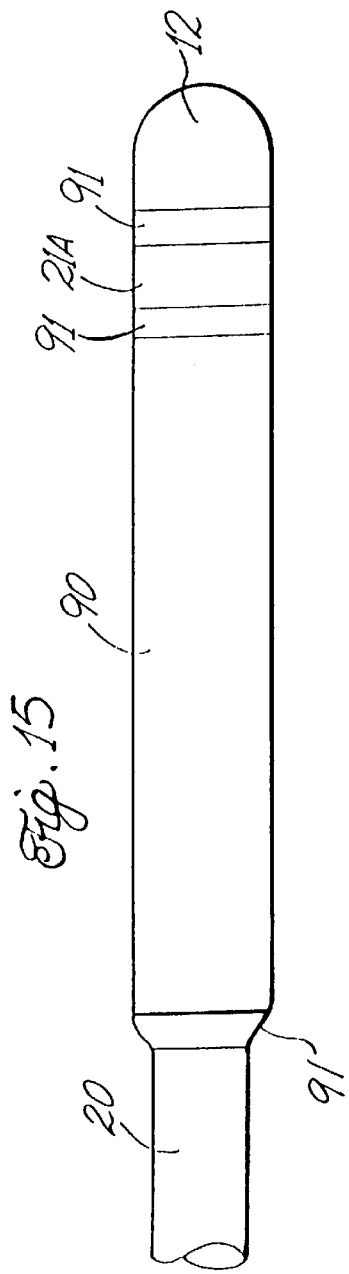

CATHETER WITH AN ELECTROMAGNETIC GUIDANCE SENSOR

RELATED APPLICATION

This application claims priority to U.S. Provisional Patent Application Ser. No. 60/000,157; filed Jun. 12, 1995.

FIELD OF THE INVENTION

This invention relates to steerable catheters for use in a vessel, and more specifically to an electrode catheter having a steerable tip and an electromagnetic sensor at the distal tip.

BACKGROUND OF THE INVENTION

Electrode catheters have been in common use in medical practice for many years. They are used to stimulate and map electrical activity in the heart and to ablate sites of aberrant electrical activity.

In use, the electrode catheter is inserted into a major vein or artery, e.g., femoral artery, and then guided into the chamber of the heart which is of concern. Within the heart, the ability to control the exact position and orientation of the catheter tip is critical and largely determines how useful the catheter is.

Steerable tip electrode catheters are now well known. Such a catheter generally has a control handle at its proximal end for controlling deflection of the tip in one or more directions. For example, U.S. Pat. Nos. 4,960,134 and Re. 34,502 to Webster disclose a particularly useful steerable tip catheter, the disclosures of which are hereby incorporated by reference. This catheter comprises a puller wire which extends on-axis through an elongated reinforced catheter body and then off-axis in a deflectable tip portion. In this arrangement, longitudinal movement of the puller wire relative to the catheter body results in deflection of the catheter tip portion. The catheter body tends not to deflect for two reasons. First, it is reinforced and therefore resists compression. Second, the puller wire extends coaxially within the catheter body. The compressive forces on the catheter body are generally uniformly distributed across the catheter body and deflection is thereby minimized. This allows precise rotational control of the catheter body and tip.

Another example of a steerable catheter can be found in U.S. Pat. No. 5,431,168 to Webster, the disclosure of which is hereby incorporated by reference. In this patent, a triple lumen catheter is disclosed. The catheter comprises an elongated catheter body, a tip portion at the distal end of the catheter body and a control handle at the proximal end of the catheter body. Three lumens extend through the catheter body and tip portion. The first lumen has a diameter of at least about one third and preferably at least about one half the outer diameter of the catheter body. The first lumen is open at the distal end of the tip portion. The first lumen provides a pathway for the passage of fluids through the catheter, or movement of a mechanical element, such as an optic fiber, anchoring wire or the like, through the catheter. The second and third lumens are off-axis. The second lumen comprises an elongated, flexible, but noncompressible tightly wound coil spring fixedly disposed within the portion of the second lumen extending through the catheter body. A puller wire is slidably mounted within and extends through the coil spring into the tip portion. The distal end of the puller wire is fixedly attached to the tip portion at or adjacent to the distal end of the tip portion. The proximal end of the puller wire is attached to the control handle for moving the puller wire longitudinally relative to the catheter body and coil spring. By this arrangement, longitudinal movement of the puller wire relative to the catheter body and coil spring results in deflection of the catheter tip with minimal and preferably no deflection of the catheter body. The third lumen also extends through the catheter body and tip portion and provides a passageway for electrode lead wires. The electrode lead wires extend from the electrodes carried on the tip portion through the catheter body and control handle to one or more plugs which are electrically connected to an electrical stimulator and/or recorder, an RF energy source or the like.

U.S. Pat. No. 5,391,199 to Ben-Haim, discloses an electrode catheter with an imaging system for the treatment of cardiac arrhythmias, the disclosure of which is hereby incorporated by reference. The system comprises an electrode catheter with an electromagnetic sensor at the distal tip of the catheter. The patent, however, does not teach how to manufacture a steerable catheter with the electromagnetic sensor. The electromagnetic sensor has a relatively large outside diameter of about 6 to 7 French (1 French=0.012 inch). This large diameter creates numerous difficulties in designing a catheter that is steerable. Additionally, the sensor has to be completely insulated from the electrodes and electrode lead wires to perform properly.

Therefore, it is desirable to have a steerable catheter which incorporates an electromagnetic sensor like the one described in U.S. Pat. No. 5,391,199 that allows the operator to steer the catheter into position while monitoring the three dimensional images of the heart generated by the use of the electromagnetic sensor.

SUMMARY OF THE INVENTION

The present invention is a steerable electrophysiology catheter (an electrode catheter) having an electromagnetic sensor designed internally into the tip portion. The catheter is a size 7 French or 8 French metal braided construction with preferably three lumens. The catheter has a deflectable tip utilizing an offset lumen with a puller wire, a noncompressible coil in the body section and a compressible Teflon sheath in the tip section. The coil is glued to the body section at both ends of the coil. The puller wire is slidably disposed within the coil and extends to the flexible tip section such that proximal movement of a puller wire deflects the tip section but the coil keeps the body from compressing and deflecting. The puller wire is soldered to a tip electrode and runs axially to a control handle. The electromagnetic sensor is mounted internally in the catheter tip by a combination of a hole drilled in the three lumen tip and a hollow bridging tube that connects the three lumen tip with the tip electrode. On the bridging tube is optionally mounted one or more ring electrodes adjacent to the tip electrode. The tip electrode has a stem and is secured to the end of the bridging tube by an etched Teflon ring which mates the electrode stem to the inside of the bridging tube. The bridging tube can be made from polyamide tubing, polyimide tubing, plastic filament impregnated composite, or other suitable thin walled non metallic material.

The lead wires from the electromagnetic sensor are disposed in a plastic covered shielded cable which is placed within a second lumen in the catheter. The electrode lead wires pass around the sensor within the bridging tube and are disposed within the third lumen in the catheter.

BRIEF DESCRIPTION OF THE DRAWINGS

These and other features and advantages of the present invention will be better understood by reference to the following detailed description when considered in conjunction with the accompanying drawings wherein:

FIG. 1 is a plan view of a catheter of the present invention;

FIG. 2 is an exploded rear perspective view of the catheter of the present invention;

FIG. 3 is a longitudinal partial cross section schematic view of the present invention;

FIG. 4 is a schematic view of a preferred control handle section of the present invention;

FIG. 5 is a cross section of the present invention as illustrated in FIG. 1 at line 5—5;

FIG. 6 is a cross section of the present invention as illustrated in FIG. 1 at line 6—6;

FIG. 7 is a schematic view of the catheter body of the present invention illustrating the noncompression coil and puller wire assembly;

FIG. 8 is a plan view of a tip electrode of the present invention with accompanying tip electrode lead wire;

FIG. 9 is a end view of the tip electrode of FIG. 8 without the electrode lead wire attached;

FIG. 10 is a cross section of the tip electrode with a puller wire attached along plane 10—10 of FIG. 9;

FIG. 11 is a cross section of the tip electrode with a thermocouple attached along plane 11—11 of FIG. 9;

FIG. 12 is a schematic view of an alternate embodiment of the electromagnetic sensor assembly of the present invention;

FIG. 13 is a cross section of the electromagnetic sensor assembly of FIG. 12 along line 13—13;

FIG. 14 is a plan view of a first bridging tube of the electromagnetic sensor assembly of FIG. 12; and FIG. 15 is a plan view of the distal end of an electromagnetic steerable catheter with a second bridging tube attached.

DETAILED DESCRIPTION

As illustrated in the drawings, the present invention is directed to a steerable cardiac electrode catheter that incorporates an electromagnetic sensor at its distal end. An electromagnetic sensor 18 or 18A suitable for use in the present invention is available from Biosense, Inc., Orangeburg, N.Y., and is described in U.S. Pat. No. 5,391,199, the disclosure of which is incorporated herein by reference. The steerable catheter is divided into three main sections which correspond to three primary subassemblies: a control handle section or subassembly 101, a catheter shaft section or subassembly 102, and an electromagnetic sensor section or subassembly 103.

The catheter is constructed by first assembling the shaft section, then assembling the electromagnetic sensor section and then assembling the control handle section.

I. SHAFT SUBASSEMBLY

A suitable catheter shaft 102 comprises a catheter body 107 (see FIG. 7) and a deflectable tip 20 and is a multiple lumen catheter of metal braided construction. A particularly suitable multilumen catheter shaft construction is disclosed in U.S. Pat. No. 5,431,168, the disclosure of which is hereby incorporated by reference. Briefly, the catheter comprises an elongated catheter body 107 having proximal and distal ends. A catheter deflectable tip portion 20 extends from the distal end of the catheter body and a control handle 201 (see FIG. 4) is provided at the proximal end of the catheter body. With reference to FIGS. 5, 6, and 7, the catheter shaft including the catheter body and tip portion comprises first, second and third lumens 22, 24 and 26 respectively. As detailed below, lumen 22 is relatively large (about 0.036 inch in diameter) and lumens 24 and 26 are relatively small (about 0.022 inch in diameter). Lumen 22 is used to carry an electromagnetic sensor cable 30 for the electromagnetic sensor 18 of the present invention. The electromagnetic sensor 30 cable comprises multiple electrode wires encased within a plastic covered shield. Lumen 24, which is off-axis is used to carry a puller wire 32, and lumen 26 is used to carry electrode lead wires and thermocouple wires 34 and 34A.

The length and diameter of the catheter body 107 are not critical and may vary according to the application, however the diameter must be large enough to accommodate the electromagnetic sensor 18 or 18A which has an outer diameter of about 6 to 7 French. For the cardiovascular catheter shown in the accompanying drawings, a length of about 40 to 48 inches and an outer diameter of about 8 French is preferred.

The catheter tip portion 20 preferably has a short length of about 5 to 7 inches. The diameter is preferably about the same as that of the catheter body 107 or slightly less (e.g., 7 French) than the diameter of the catheter body 107 (as shown in FIG. 7).

The catheter body 107 and tip portion 20 may be made of any suitable non-toxic material. In a preferred embodiment, the catheter body 107 and tip portion 20 comprise a single elongated tubular extrusion made of a thermoplastic resin such as polyurethane. One or more layers of a reinforcing braided mesh 28 (see FIG. 5) of, for example, stainless steel or dacron, overlie the polyurethane extrusion in the catheter body portion 107. The reinforcing mesh 28 is, in turn, coated with a layer of polyurethane or other suitable plastic material.

It is understood that, if desired, the catheter body 107 and tip portion 20 may be separate sections of appropriate tubular material joined together rather than a single extrusion. If separate sections of tubular material are joined together, the construction of the catheter body 107 need not be the same as that of the tip portion 20. For example, the catheter body 107 may be reinforced with one or more layers of stainless steel mesh, whereas the tip portion may be reinforced with dacron mesh or simply be unreinforced to increase flexibility (as shown in FIG. 6).

Turning to FIG. 7, a presently preferred catheter shaft 102 is illustrated. The catheter body 107 is about an 8 French diameter body that extends for about 40 inches. The body tapers at taper 108 to the tip portion 20 which is about 7 French and extends for about 6 inches. At the distal end of the tip portion, a 4 mm deep 0.063 inch diameter hole 36 is drilled and then smoothed out. Two noncompressible coil glue holes 43 and 44 are drilled into the catheter shaft into lumen 24, one at the distal end in the catheter body 102 about 3 inches from the distal tip and one at the proximal end in the catheter tip about ⅜ inch to about ½ inch from the proximal end. A noncompressible coil 41, slightly smaller than the diameter of lumen 24 is inserted into the lumen until the distal end 42 of the coil is about ½ inch distal to the glue hole 44 and the proximal end 45 extends proximally out of the catheter shaft 102. The noncompressible coil 41 has an outer diameter of about 0.02 inch and an inner diameter of about 0.01 inch. A polytetrafluorethylene (Teflon®) coated 0.007 inch stainless steel puller wire 32 is then inserted into the noncompressible coil 41. The puller wire 32 is substantially longer than the noncompressible coil 41 such that the proximal and distal ends of the puller wire 32 can be secured to the control handle 201 and the tip electrode 12 respectively later during the manufacturing process. The noncompressible coil 41 is then secured in place by applying glue such as polyurethane in both glue holes 43 and 44 until it wicks over about ½ inch to about ¾ inch long areas. The glue is cured in a warm air oven.

II. ELECTROMAGNETIC SENSOR SUBASSEMBLY

The next step in the manufacturing process is to assemble the electromagnetic sensor subassembly 103. First, the Teflon® coating over the puller wire 32 is stripped off at its distal end for about 2 cm. A 3.5 mm long 27 gage stainless steel hollow crimping tube 50 is then crimped onto the distal end of the puller wire 32 (see FIG. 10).

Three 6 feet long #38 copper electrode insulated lead wires 34 and one 6 feet long #38 constantan thermocouple insulated lead wire 34A are placed inside lumen 26 of the catheter shaft (as shown in FIGS. 5 and 6). All of the lead wires 34 and 34A are insulated with the insulation being stripped approximately one inch from the distal end of wires 34 and 34A. Using one of the copper lead wires 34 and the constantan lead wire 34A a thermocouple 57 is constructed by twisting the distal ends together, about one turn per millimeter. The twisted lead wires are then tinned with 25% indium Litton Kester Solder SN96AG04 and Staykleen flux. The twisted lead wires are then cut to approximately 1 mm in length to complete the thermocouple 57 and inserted into a piece of 0.014 inch inner diameter and 0.016 inch outer diameter tube 61 (see FIG. 11) that is about 2½ to 3 mm long. The tube 61 is preferably constructed out of polyimide, but other well known materials could be used. The twisted wires are then secured within the tube 61 with epoxy.

The next step of the manufacturing process is to construct the first bridging tube 16. In the embodiment illustrated in FIGS. 2 and 3, there is only one bridging tube 16 which is a cylindrical 0.093 inch inner diameter and 0.098 inch outer diameter polyimide tube about 15 mm long. The bridging tube 16 may be made from other materials such as polyamide tubing, plastic filament impregnated composite, or other suitable non-metallic weldable material. In the embodiment illustrated in FIGS. 12, 13 and 14, the first bridging tube 16A is constructed out of a piece of 0.080 inch inner diameter and 0.086 inch outer diameter polyimide tube about one inch long. The polyimide tube is then placed over a stepped mandrel with a larger diameter of 0.077 inch and a smaller diameter of 0.050 inch. A 0.0065 inch monel or manganin wire is then wrapped around the proximal end of the polyimide tube over the smaller diameter section of the mandrel to reduce the diameter and to create taper 70 and smaller diameter section 75. The polyimide tube is then heated at 150° C. for about 5 minutes such that it will retain its new shape. The small diameter section 75 of the polyimide tube is then cut to about 3 mm in length and the large diameter section is cut to about 12 mm in length such that the overall length is about 15 mm. The bridging tube 16A is then removed from the mandrel.

A lead wire hole 71 is optionally punched in the distal large diameter side of the bridging tube 16 or 16A about 1 to about 1½ mm from the distal edge (see FIGS. 3 or 14). One of the electrode lead wires 34 is then inserted through the proximal end of the bridging tube and out through the lead wire hole 71. The insulation is striped of the distal end of the lead wire and is then soldered onto an optional ring electrode 21A. The ring electrode 21A is then placed over the bridging tube 16A about ½ mm from the distal edge (see FIGS. 2, 3, and 12). The ring electrode 21A is glued in place using a small amount of glue such as polyurethane and then cured in a warm air oven.

Next, the thermocouple 57, puller wire 32, and one of the tip electrode lead wire 34 are inserted all the way through the bridging tube.

A tip electrode 12 is then made out of a solid platinum or solid platinum iridium alloy bullet shaped member (see FIGS. 2, 8, 10, and 11) that is about 7 French in diameter. The proximal end of the bullet shaped tip electrode 12 is machined such that a cylindrical stem 54 about 2 mm long is created. The center of the stem is drilled out such that the stem 54 is hollow on its proximal side. An electrode lead wire hole 55 is then drilled into the side of the stem about ½ mm from the proximal end of the stem 54 (see FIGS. 2, 8, and 10). Three holes are then drilled into the body 12 of the tip electrode: a puller wire hole 51, a thermocouple hole 52 and a vent hole 53 (see FIGS. 9, 10 and 11). The puller wire hole 51 (see FIG. 10) is drilled parallel to the axis of the tip electrode about 2 mm deep and about ½ mm wide. The thermocouple hole 52 (see FIGS. 9 and 11) is about ½ mm wide and is drilled about 90° away from the puller wire hole 51 and at about 30° to the axis of the tip electrode 12 such that the thermocouple hole 52 traverses through the central axis of the tip electrode 12. Care is taken to ensure that the thermocouple hole 52 does not extend out the side of the tip electrode 12. The vent hole 53 is also about ½ mm wide and is drilled 180° away from the thermocouple hole 52 and is drilled at about a 45° angle to the axis of the tip electrode 12 such that the vent hole 53 intersects with the thermocouple hole 52.

As illustrated in FIG. 8, one of the electrode lead wires 34 is inserted through the hollow distal stem 54 of the tip electrode 12 and through the lead wire hole 55. The insulation on this electrode lead wire 34 is stripped off its distal end and then wrapped about 3 to about 5 times around the stem 54 and soldered into place at point 38.

Next, the puller wire 32 with the 27 gage crimping tube 50 crimped to the puller wire's distal end are inserted into the puller wire hole 51. Preferably just prior to the insertion of the puller wire 32 and the crimping tube 50 into the puller wire hole 51 a small amount of soldering material 56 is placed in the puller wire hole. The puller wire 32 and crimping tube 50 are then soldered into the puller wire hole 51 using additional soldering material 56.

Next, the thermocouple tube 61 is inserted into the bottom of the thermocouple hole 52. Epoxy 62 is then applied into the vent hole 53 until it appears in the thermocouple hole. The epoxy is cured in a warm air oven for about one hour.

An etched Teflon ring 14 that is 2 mm long is then inserted over the stem 54 of the tip electrode (see FIG. 2). The electrode lead wire 34 connected to the stem 54 of the tip electrode is bent back distally and is directed to the thermocouple hole and thermocouple lead wires. All of the lead wires 34 and 34A are collected together and travel around the outside of the Teflon ring 14 as best illustrated in FIG. 2. The Teflon ring 14 is then glued to the tip electrode 12 using polyurethane or the like and cured in a warm air oven. The tip electrode lead wires 34 and the thermocouple lead wire 34A are then carefully welded together using polyurethane and cured in a warm air oven.

The next step is to insert an electromagnetic sensor 18 or 18A into the cavity 25 (see FIGS. 2, 3, and 12) defined by the bridging tube 16 or 16A while aligning the optional ring electrode lead wire with the three other lead wires 34. As illustrated in FIGS. 2 and 3, the electromagnetic sensor 18 of this embodiment comprises two portions of different diameter, the first diameter portion 17 being smaller in diameter than the second diameter portion 19. A sensor cable 30 extends out of the smaller first diameter 17 and includes the electrode lead wires needed for the operation of the electromagnetic sensor. In an alternate embodiment illustrated in FIGS. 12–15, the electromagnetic sensor 18A is uniform in diameter and is approximately 7 French in diameter with the sensor cable 30 extending from the center of the proximal end of the sensor. As illustrated in FIG. 13, the lead wires 34 and 34A are arranged at an angle α of about 90° apart from the puller wire 32 in an orientation which will align them with the appropriate lumen in the catheter body 107. An etched piece of Teflon® tube 66, 2 mm long, is then installed over the sensor cable 30 and slid down inside the proximal end of the bridging tube 16A (see FIG. 12). The electromagnetic sensor 18A is potted in the bridging tube 16A using polyurethane. The tip electrode 12 with the Teflon® ring 14 attached is then installed into the distal end of the bridging tube 16A. All electrode lead wires 34 and 34A, the sensor cable 30 and the puller wire 32 are oriented as shown in FIG. 13 and the polyurethane is allowed to cure in a warm air oven.

In the embodiment illustrated in FIGS. 2 and 3, the electromagnetic sensor 18 has a reduced diameter portion 17 that is proximal to a larger diameter portion 19. The tip electrode 12, with electrode lead, thermocouple, and puller wires 34, 34A, and 32, respectively, attached, is made similarly as described above. The bridging tube 16 is then inserted over the electrode lead wires 34, thermocouple lead wire 34A and puller wire 32 such that the Teflon ring 14 fits within the distal end of the bridging tube 16. The puller wire 32 and electrode and thermocouple lead wires 34 and 34A are oriented 90° apart and the electromagnetic sensor 18 is placed within the bridging tube 16. The electromagnetic sensor 18 and Teflon ring 14 are then potted with polyurethane and allowed to cure in a warm air oven.

III. INSTALL ELECTROMAGNETIC SENSOR SUBASSEMBLY TO SHAFT SUBASSEMBLY

The next step of the manufacturing process is to install the electromagnetic sensor subassembly 103 into the shaft subassembly 102. In the embodiments of FIGS. 2 and 3, the reduced diameter 17 of the electromagnetic sensor fits into the drilled hole 36 in the distal end of the tip portion 20 the catheter body 107. Care is taken to make sure that all the electrode lead wires 34A and thermocouple wire 34A are in lumen 26 of the catheter body 107, the puller wire 32 is in lumen 24 of the catheter body 107, and the electromagnetic sensor cable 30 is in lumen 22 of the catheter body 107. Preferably, a compressible Teflon sheath 39 is inserted over distal portion of the puller wire 32 within lumen 24 and to the tip electrode 12 to provide a smooth channel for the movement of the puller wire 32.

Once the locations of all the wires and cable are confirmed in their proper lumens, the proximal end of the electromagnetic sensor 18 is placed within the drilled hole 36 and potted with polyurethane. If the optional compressible tube 39 is in place, care is taken to ensure that no polyurethane enters the tube 39. All wires and the cable are pulled taut and the polyurethane is allowed to cure in a warm air oven.

In the embodiment illustrated in FIG. 15, a second bridging tube 90 approximately 15 mm long with an outer diameter of about 0.098 inch and an inner diameter of about 0.093 inch is slid over the distal end of the tip portion 20 of the catheter body 107. The reduced diameter section 75 of the first bridging tube 16A is inserted in the drilled hole 36 in the distal end of the tip portion 20 of the catheter body 107 (as shown in FIG. 2).

Care is again taken to ensure that the lead wires 34 and thermocouple wire 34A are contained within lumen 26. The distal section of the puller wire 32 is inserted into a compressible sheath 39, preferably made out of Teflon. The compressible sheath 39 covers the puller wire 32 over the distance from the tip electrode 12 to the noncompressible coil 41 in lumen 24. All the lead wires 34 and 34A and the electromagnetic sensor cable 30 are pulled taut. Polyurethane is then potted over the first bridging tube 16A and over the distal end of the tip portion 20 of the catheter body 107. The second bridging tube 90 is then pulled distally such that the junction between the catheter shaft section 102 and the electromagnetic sensor section 103 is contained within the second bridging tube 90 and the distal end of the second bridging tube is about 2 mm proximal to the ring electrode 21A. The polyurethane is then allowed to cure in a warm air oven. All margins around the second bridging tube, ring electrode, and tip electrode are smoothed out with the addition of polyurethane 91 (see FIG. 15) and the catheter is allowed to completely cure in a 100° C. oven for two hours.

IV. CONTROL HANDLE ASSEMBLY

As discussed above, the puller wire 32 is soldered to the tip electrode 12, runs outside the Teflon sheath 14, through the bridging tube 16 or 16A around the electromagnetic sensor 18 or 18A, into lumen 24, and runs to a control handle 201 (see FIG. 4) located at the proximal end of the catheter body. The control handle 201 should have means for controlling the longitudinal movement of puller wire 32 with respect to the axis of the catheter body 107. A suitable control handle is disclosed in U.S. Pat. Nos. 4,960,134 and Re. 34,502, the disclosures of which are incorporated by reference. The puller wire 32 is preferably coated with any suitable electrically insulating and lubricating material, such as polytetrafluoroethylene. The puller wire 32 is installed to the piston (not shown) within the control handle as described in U.S. Pat. Nos. 4,960,134 and Re. 34,502. The proximal end of the catheter body 107 is also installed within the control handle 201.

In the preferred embodiment, the control handle 201 is modified from the one described in U.S. Pat. Nos. 4,960,134 and Re. 34,502 in that it has a threaded end 202 with a barrel extension 203 threaded into the threaded end. The barrel extension 203 contains a printed circuit board 204 for processing signals to and from the electromagnetic sensor 18 or 18A. The electromagnetic sensor cable 30 is connected to the printed circuit board 204. The printed circuit board 204 is manufactured to correspond to the electromagnetic sensor 18 or 18A and is available from Biosense, Inc. The printed circuit board 204 is protected from magnetic fields via a metal via a metal magnetic shield 205. Care is taken to ensure that the thermocouple wires 34A and one of 34 are passed within the magnetic shield 205 and the electrode lead wires 34 pass outside the magnetic shield 205.

At the proximal end of the barrel extension 203 is a cable adaptor 207 where lead wires to and from the printed circuit board 204 are attached, the electrode lead wires are attached, and the thermocouple wires are attached. A conductor 208 is connected to the cable adaptor 207 and is then ready to be connected to a processing and controlling unit as described in U.S. Pat. No. 5,391,199.

The importance of this above-described design is that the three lumens 22, 24 and 26 in the catheter body 107 provide a catheter core structure which supports the metallic braid providing high torque, and a lumen for the noncompressible coil 41 allowing for good catheter flexibility without compressive waviness when the puller wire 32 is pulled. Proximal movement of the puller wire 32 with respect to the catheter body 107 results in the deflectable tip section 20 bending in one direction. Thus the electromagnetic sensor catheter is steerable by controlling the movement of the puller wire 32 with the control handle 201.

The preceding description has been presented with references to presently preferred embodiments of the invention as shown in the drawings. Persons skilled in the art and technology to which this invention pertains will appreciate that alterations and changes in the described structures can be practiced without meaningfully departing from the principle, spirit and scope of this invention. Accordingly, the foregoing description should not be read as pertaining only to the precise structures described and shown in the accompanying drawings, but rather as consistent with and as support for the following claims which are to have their fullest and fairest scope.

What is claimed is:

1. A steerable electromagnetic sensor catheter comprising:
   a control handle;
   a catheter shaft comprising proximal and distal ends and a plurality of lumens wherein the distal end is deflectable and the proximal end of the catheter shaft is connected to the control handle;
   an electromagnetic sensor with proximal and distal ends wherein the proximal end of the sensor is adjacent to the distal end of the catheter shaft;
   an electromagnetic sensor cable connected to the electromagnetic sensor wherein the sensor cable is disposed within one of the catheter shaft lumens and is connected to the control handle;
   a tip electrode adjacent to the distal end of the sensor having a corresponding electrode lead wire attached which runs through one of the shaft lumens and is connected to the control handle;
   a puller wire having proximal and distal ends wherein the proximal puller wire end is connected to the control handle and the distal puller wire end is connected to the tip electrode, and wherein the puller wire extends through one of the shaft lumens;
   a noncompressible coil within the lumen through which the puller wire extends in surrounding relation to the puller wire from about the proximal end of the catheter shaft to a location spaced apart from the distal end of the catheter shaft, said compression coil being fixedly attached at its proximal and distal ends to the catheter shaft; and
   a bridging tube glued to the distal end of the catheter shaft and to the tip electrode, wherein the electrode lead wire and the electromagnetic sensor are glued within the bridging tube and the puller wire is slidably retained within the bridging tube.

2. The electromagnetic sensor catheter of claim 1 comprising a compressible tube slidably covering a distal portion of the puller wire from the distal end of the noncompressible coil to the tip electrode, and the compressible tube is glued within the bridging tube.

3. The electromagnetic sensor catheter of claim 1 wherein the catheter shaft has three lumens.

4. The electromagnetic sensor catheter of claim 3 wherein one of the three lumens is relatively larger than the other two lumens.

5. The electromagnetic sensor catheter of claim 4 wherein the larger lumen contains the electromagnetic sensor cable; one of the two smaller lumens contains the noncompression coil, the puller wire and part of the compressible tube; and the other smaller lumen contains the tip electrode lead wire.

6. The electromagnetic sensor catheter of claim 1 further comprising a thermocouple attached within the tip electrode wherein the thermocouple has two lead wires attached which run through one of the shaft lumens and are connected to the control handle.

7. The electromagnetic sensor catheter of claim 6 wherein the thermocouple wires are grouped with the tip electrode lead wire and run through the same shaft lumen.

8. The electromagnetic sensor catheter of claim 1 further comprising a ring glued between the tip electrode and the electromagnetic sensor and glued within the bridging tube.

9. The electromagnetic sensor catheter of claim 1 further comprising at least one ring electrode attached to the outside of the bridging tube and a corresponding ring electrode lead wire attached to the ring electrode and to the control handle wherein the ring electrode lead wire runs through one of the shaft lumens.

10. The electromagnetic sensor catheter of claim 1 further comprising a printed circuit board disposed within the control handle and connected to the sensor cable wherein the printed circuit board helps to control the input and output of the electromagnetic sensor.

11. A steerable electromagnetic sensor catheter comprising:
    an elongated catheter body having proximal and distal ends;
    a flexible tip portion connected to the distal end of the catheter body having proximal and distal ends;
    at least one lumen extending lengthwise through the catheter body and the tip portion;
    a tip electrode connected to the distal end of the tip portion and having an electrode lead wire attached to the tip electrode which extends through one of the at least one lumen to the proximal end of the catheter body.
    a bridging tube located at the distal end of the tip portion, the bridging tube having a distal end connected to the tip electrode and a cavity communicating with one of the at least one lumen in the flexible tip portion wherein the tip electrode lead wire passes through the cavity in the bridging tube.
    an electromagnetic sensor contained within the tip portion adjacent to the distal end of the tip portion, at least a portion of the electromagnetic sensor being disposed in the bridging tube;
    an electromagnetic sensor cable having a distal end connected to the electromagnetic sensor and extending through one of the at least one lumen to the proximal end of the catheter body; and
    a puller wire having a distal end fixedly attached to the tip portion, the puller wire extending through one of the at least one lumen to the proximal end of the catheter body, wherein longitudinal movement of the puller wire relative to the catheter body results in deflection of the tip portion.

12. The steerable electromagnetic sensor catheter according to claim 11 in which the distal end of the puller wire is connected to the tip electrode.

13. The steerable electromagnetic sensor catheter according to claim 11 in which the puller wire extends through the cavity in the bridging tube and is connected to the tip electrode.

14. The steerable electromagnetic sensor catheter according to claim 11 in which the electromagnetic sensor is glued into the cavity in the bridging tube.

15. The steerable electromagnetic sensor catheter according to claim 11 further comprising a noncompressible coil having a proximal end and a distal end, the noncompressible coil surrounding the puller wire between the proximal and distal ends of the catheter body.

16. The steerable electromagnetic sensor catheter according to claim 15 in which the at least one lumen containing the puller wire is an off-axis lumen.

17. The steerable electromagnetic sensor catheter according to claim 15 further comprising a compressible tube slidably covering the puller wire from the distal end of the noncompressible coil to the distal end of the puller wire.

18. The steerable electromagnetic sensor cathether according to claim 13 further comprising a compressible tube slidably covering the puller wire from the tip electrode to at least the proximal end of the bridging tube.

19. The steerable electromagnetic sensor cathether according to claim 18 in which the compressible tube is glued into the cavity in the bridging tube.

20. The steerable electromagnetic sensor catheter according to claim 11 in which the at least one lumen containing the puller wire is off-axis in the tip portion.

21. The steerable electromagnetic catheter according to claim 20 in which the at least one lumen containing the puller wire is in generally co-axial relation to the catheter body.

22. The steerable electromagnetic sensor catheter according to claim 11 further comprising a control handle attached to the proximal end of the catheter body.

23. The steerable electromagnetic sensor catheter according to claim 22 in which the control handle further comprises means attached to the proximal end of the puller wire for causing longitudinal movement of the puller wire in order to deflect the tip portion.

24. The steerable electromagnetic sensor cathether according to claim 22 in which the control handle is attached to the sensor cable.

25. The steerable electromagnetic sensor cathether according to claim 24 in which the control handle contains means attached to the sensor cable for processing signals to and from the electromagnetic sensor.

26. The steerable electromagnetic sensor catheter according to claim 11 further comprising at least one ring electrode attached to the outside of the bridging tube and a corresponding ring electrode lead wire attached to the ring electrode and passing through one of the at least one lumen to the proximal end of the catheter body.

* * * * *